United States Patent [19]
Linder

[11] Patent Number: 5,749,357
[45] Date of Patent: May 12, 1998

[54] MALLEABLE INTRODUCER

[76] Inventor: Gerald S. Linder, P.O. Box 1085, Pacific Palisades, Calif. 90272

[21] Appl. No.: 445,368

[22] Filed: May 19, 1995

[51] Int. Cl.⁶ ................................................ A61M 16/00
[52] U.S. Cl. .................... 128/200.26; 128/207.14; 128/207.15
[58] Field of Search .................. 128/200.26, 207.14, 128/207.15

[56] References Cited

U.S. PATENT DOCUMENTS

| | | | |
|---|---|---|---|
| 3,957,055 | 5/1976 | Linder et al. | 128/200.26 |
| 3,996,939 | 12/1976 | Sheridan et al. | 128/207.14 |
| 4,185,639 | 1/1980 | Linder | 128/200.26 |
| 4,261,339 | 4/1981 | Hanson et al. | 606/194 |
| 4,351,330 | 9/1982 | Scarberry | 128/207.15 |
| 4,471,779 | 9/1984 | Antoshkiw et al. | |
| 4,655,214 | 4/1987 | Linder | 128/207.14 |
| 4,716,896 | 1/1988 | Ackerman | 128/207.14 |
| 4,819,619 | 4/1989 | Augustine et al. | 128/200.26 |
| 4,865,586 | 9/1989 | Hedberg | 128/200.26 |
| 4,913,139 | 4/1990 | Ballew | 128/200.11 |
| 4,938,746 | 7/1990 | Etheredge, III et al. | 128/200.26 |
| 5,038,766 | 8/1991 | Parker | 128/200.26 |
| 5,108,366 | 4/1992 | Schatz | 604/55 |
| 5,108,374 | 4/1992 | Lemieux | 604/164 |
| 5,127,905 | 7/1992 | Lemieux | 604/164 |
| 5,179,963 | 1/1993 | Berger | 128/898 |
| 5,235,970 | 8/1993 | Augustine | 128/200.26 |
| 5,242,429 | 9/1993 | Nwaneri et al. | 604/270 |
| 5,257,620 | 11/1993 | Schermerhorn | 128/200.26 |
| 5,273,527 | 12/1993 | Schatz et al. | 604/43 |
| 5,295,493 | 3/1994 | Radisch, Jr. | 128/772 |
| 5,329,921 | 7/1994 | Socaris et al. | 128/207.14 |
| 5,339,805 | 8/1994 | Parker | 128/200.26 |
| 5,341,803 | 8/1994 | Goldberg et al. | 128/632 |

OTHER PUBLICATIONS

Seiji Watanabe, M.D., Ph.D., et al; Anesth Analg 1994;78; A "Bubble-Tip" (Airguide®) Tracheal Tube System: Its Effects on Incidence of Epistaxis and Ease of Tube Advancement in the Subglottic Region During Nasotracheal Intubation; Feb. 18, 1994; pp. 1140–1143.

*Primary Examiner*—Aaron J. Lewis

[57] ABSTRACT

An introducer for guiding an endotracheal catheter or the like incorporates a malleable introducer tube with a smooth, inflatable introducer tip. In order to provide intubation with least trauma and greatest catheter configuration and tip control, an introducer is provided having a malleable and shape-retaining tube along at least a portion of the length intermediating the smooth, inflatable sheath at the tip of the introducer and the clamp or other fluid flow control means maintaining the inflated state of the sheath. In one embodiment, intermediation of the length between the sheath and the clamp is made almost entirely by a malleable tube made of a ductile metal such as aluminum. The tube may be thick-walled to reduce the volume necessary to inflate the sheath. In another embodiment, only the introducer tip may be of a malleable metal, such as copper. Significant advantages are offered by the use and inclusion of resilient, malleable portions in the introducer.

17 Claims, 2 Drawing Sheets

MALLEABLE INTRODUCER

BACKGROUND OF THE INVENTION

1. Field of the Invention

This invention relates to endotracheal catheters, and more particularly to introducers for the intubation of such catheters into the patient. Specifically, the present invention is directed towards a malleable introducer tube having a smooth, inflatable sheath at its distal end.

2. Description of the Related Art

A wide variety of catheters are available to the practicing physician for intubation into the different passageways of a patient as the need arises. Catheters vary in size, length, type, and texture of material of which they are composed.

Of importance to the anesthesiologist is the class of catheter known in the art as endotracheal tubes designed for intubation into the trachea of a patient prior to anesthesia, in emergency situations such as those requiring resuscitation, and for life support. Endotracheal tubes may be of the cuffed or uncuffed type, the uncuffed type being a smooth, long, hollow, pliable tube having open proximal and distal ends. The conventional cuffed endotracheal tube is provided with an inflatable cuff or balloon surrounding the outside distal end portion of the tube at a position above the distal tip. The ends of the cuff are secured to the outside wall of the tube to provide a fluidtight seal between the outside wall and the inside of the cuff. After intubation of a cuffed tube, the cuff is expanded by applying air (or other non-toxic fluid) under pressure to ensure that the outside wall of the cuff embraces the trachea of the patient.

The distal tip, or end, of conventional catheters and endotracheal tubes is usually beveled at an angle which may vary between 30 to 60 degrees, depending, in part, upon the type of catheter to be used. In addition to the beveled distal tip, certain catheters and endotracheal tubes may have a small side or lateral opening through the side wall of the catheter at the distal end portion of the tube just above the beveled tip. This latter design is referred to in the art as a Murphy tip.

Intubation of the endotracheal tube, whether cuffed or uncuffed, may be accomplished either by inserting and passing the distal end portion through the patient's mouth and down into the trachea or, under certain conditions, by inserting and passing the distal end portion through the patient's nasal passageway past the pharynx and down into the trachea. In the former case, the endotracheal tube may be of a size and type identified as an oral endotracheal tube. Endotracheal tubes, identified as either oral or nasal, may be intubated through the mouth or through the nose of the patient.

The intubation of catheters and endotracheal tubes is not without its problems. To aid the intubation of oral endotracheal tubes, the anesthesiologist may employ a catheter guide or stylet inserted within the endotracheal tube prior to intubation to enable the physician to shape the endotracheal tube, provide additional structural rigidity to the tube, and afford an improved means for gripping and maneuvering the tube to accomplish intubation. My prior U.S. Pat. Nos. 3,957,055; 4,185,639; and 4,655,214 pertain to improvements in the intubation of catheters and endotracheal tubes. These patents are incorporated herein by this reference.

Due to the highly sensitive and delicate nature of the mucous membranes lining the airway passages, larynx, and trachea, trauma and injury can be produced to the patient by the hard, open, bevel tip of endotracheal tubes. The use of an inflated balloon protruding from and filling the distal tip of the endotracheal tube during the process of intubation prevents trauma and injury.

Conventional malleable metal stylets can be preformed together with the endotracheal tube at their distal tips to a "J" shape. This often aids in intubating anteriorly or malpositioned displaced larynxes. No protection is afforded to the mucous membranes and anatomical structures, however, from the hard, open-ended bevel tip of the endotracheal tube. Protrusion of the hard, pointed stylet tip beyond the confines of the endotracheal tube distal tip may occur and cause serious injury, particularly during the course of a difficult intubation. Misdirected intubation into the esophagus has often caused serious injury or perforation.

The combination of a malleable stylet with a balloon sheath at the distal portion allows for maximum directionality while affording maximum protection. These are the paramount objectives and purposes of this invention.

The present invention is directed to improvements in the intubation of catheters and endotracheal tubes and, especially, to the intubation of orotracheal tubes by means of a malleable but shape-retaining introducer tube coupled with an inflatable sheath.

A soft, inflatable introducer having a closed, rounded, distal-tipped sheath, is inserted into the open proximal end of and through a hollow, cylindrical catheter or endotracheal tube, with the distal-tipped sheath protruding partway beyond the open distal end of the catheter. The distal-tipped sheath is inflated, prior to intubation, to a diameter equal to or slightly larger than the outer diameter of the catheter. Both catheter and introducer are intubated into and through the passageway of the patient. The inflated sheath serves not only as a guide but also as a soft and flexible opener or enlarger of the sensitive membranes within the passageway, thereby enabling the catheter to better and more safely penetrate and negotiate the varied shapes, obstacles, or bends encountered. After the catheter has been successfully intubated within the passageway through the larynx and into the trachea, for example, the distal-tipped sheath is deflated and the introducer is withdrawn.

SUMMARY OF THE INVENTION

The present invention resides in the use of malleable tubing in forming the connection between the distal inflatable tip of the introducer and its proximal end. Generally, ductile metals such as aluminum and copper may be used to form the hollow tubes that achieve such introducer rods. Similarly malleable metals, alloys, or other substances may also be used so long as they can be entirely sterilized for use in the operating theater and intimate patient contact.

Previously, only flexible and non-shape-retaining materials such as latex or other rubber, polyvinyl chloride, or other medically approved tubing have been used in order to form the hollow cylindrical tube that allows communication through the catheter between the proximal introducer end available to the physician and the distal introducer end intubated into the patient. While the use of such flexible introducers allowed for easier intubation with less trauma such as oropharyngeal bleeding or epistaxis; anomalous structures and anatomical variants such as an anteriorly positioned larynx could have prevented intubation entirely or allowed such intubation only with trauma to the patient. The inherent flexibility of both the catheter and the introducer tube prevented the physician from having any significant directional control over the end tip of the catheter with its introducer. This would sometimes limit introducer applicability for successful intubation.

Use of a rigid introducer tube is entirely inadequate as it cannot conform to the patient's internal contours. Particularly, the bends, curves, and other articulations present within the nasal and oral cavities and associated structures require that a catheter find clear passage therethrough with as little obstruction as possible.

By use of a malleable introducer tube or tip together with the inflated balloon sheath, the physician can control the shape of the catheter surrounding the introducer prior to inserting the catheter-introducer pair into the patient. Furthermore, and of great significance, is that during the intubation process, should an obstruction otherwise prevent the passage of the catheter with its introducer, the inflated, protruding balloon prevents infliction of trauma on contacted tissues and structures. As such introducer tubes can take the length of approximately 30 to 45 centimeters (approximately 12 to 18 inches), the control of the distal tip serves to provide the physician a better way to intubate the patient with less trauma, consequently reducing the stresses of surgery and facilitating patient therapy and healing.

Prior introducers were either solid malleable stylets which afforded directionality and no protection against trauma or flexible plastic tubes with balloon sheaths which provided protection, but limited directionality.

OBJECTS OF THE INVENTION

It is an object of the present invention to provide means by which a physician can control the distal end of a catheter with an introducer.

It is another object of the present invention to provide a physician means by which the shape of a catheter with introducer may be controlled in a resilient but potentially yielding manner.

It is yet another object of the present invention to provide malleable introducer means that may be sterilized completely for use in the operating theater.

It is yet another object of the present invention to provide an introducer for a catheter that is malleable at its tip.

A principal object of the present invention is to provide an improved method and apparatus for the intubation of catheters which reduce trauma and injury to the patient through use of a distal balloon sheath as well as providing better means by which catheters may be controllably articulated prior to and during intubation.

Another object is to provide a malleable, shape-retaining introducer that allows greater control over catheter configuration before and during intubation.

Still another object is to provide an improved catheter and inflatable introducer combination having a malleable introducer tube which enables the physician to more readily intubate the catheter, after which the introducer is deflated and the entire introducer assembly removed.

An important object is to provide an improved procedure for the intubation of endotracheal tubes into the oral and nasal airways of a patient by providing the physician with greater control over catheter configuration before and during intubation.

The above objects of and the brief introduction to the present invention will be more fully understood, and further objects and advantages will become apparent, from a study of the following detailed description in connection with the drawings.

DESCRIPTION OF THE PREFERRED EMBODIMENTS

Figure 1:
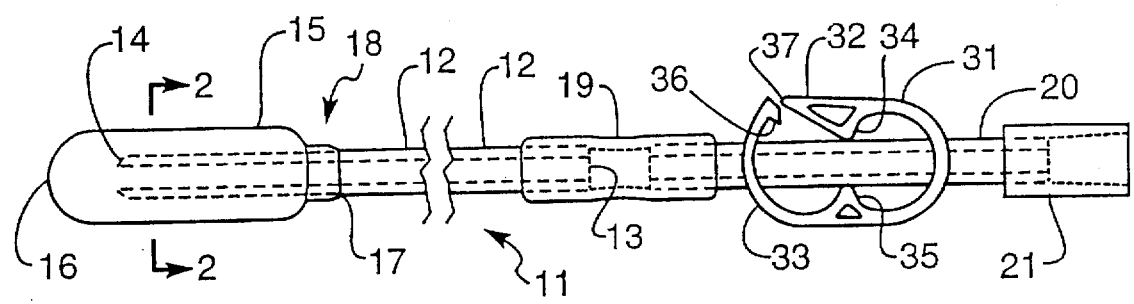
FIG. 1 shows in plan view a first embodiment of the present invention, having a malleable introducer tube.
Figure 2:
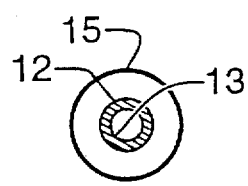
FIG. 2 shows a cross-section of the embodiment of FIG. 1 along line 2—2 of FIG. 1.

Referring to FIG. 1, the malleable introducer 11 of the invention includes a hollow, cylindrical tube 12 of malleable material, such as a ductile and medically approved malleable tubing, having an open proximal end 13 and an open distal end, or tip, 14. A hollow, cylindrically shaped sheath 15 of relatively thin material has a closed, soft, and rounded tip 16 and an end portion 17 securely attached and sealed to the outside cylindrical surface of tube 12 at position 18. A fluidtight seal exists between the inside of sheath 15 and the outside cylindrical surface of tube 12. Approximately one third of the length of sheath 15 may extend beyond the open distal end, or tip, 14 of tube 12. Approximately two thirds of the length of sheath 15 may overlay the distal end portion of tube 12, as shown. The diameter of sheath 15 is somewhat larger than the outside diameter of tube 12.

The length of tube 12 is determined by the length of the catheter or endotracheal tube for which it is to be used. The diameter of tube 12, as well as the diameter of uninflated sheath 15, is less than the inside diameter of the catheter. Preferably, the malleable tube has relatively thick walls while maintaining an unobstructed channel for fluid flow therethrough. While allowing a significant amount of bending, the thick-walled and small-channeled malleable tube 12 demands less fluid for inflating the sheath 15. Additionally, the thick walls of the tube 12 prevents it from buckling during the bending or other configuration process.

The hollow cylindrical tube 12 is preferably constructed of a malleable metal that is chemically stable and readily made sterile. Such metals include aluminum as aluminum spontaneously generates a noncorrosive and inert external layer of aluminum oxide. This aluminum oxide layer prevents any corrosion from taking place upon the hollow cylindrical tube 12. Other ductile, or malleable, metals, alloys, or materials may be used so long as they may be made sterile for use in the operating theater. Preferably, a "dead soft" type of aluminum such as annealed 3003 aluminum (as it is known in the industry) is used.

Some metals, such as copper, may require a coating of plastic about any exposed surface so as to prevent any reaction by the metal with its surrounding environment. Such a plastic coating allows a metal such as copper to maintain a pristine state while providing an inert contact surface for any materials passing through or about the hollow cylindrical tube 12. As with all other materials used for introducers, such copper or other materials should be so malleable as to be considered "dead soft."

Sheath 15 may be composed of polyisoprene, latex rubber, polyvinyl chloride, or other suitable medically approved material. Sheath 15 is designed to be inflated by fluid supplied under pressure through hollow tube 12, as described hereinafter.

Note should be taken that as set forth herein, inflation by fluid means is intended to include any available or particularly advantageous, non-toxic fluid. While such fluids may include saline solutions, nitrogen or other inert gas or gas mixture, the use of such exotic fluids may be complicated and costly. Preferably, the inflation fluid is air supplied ambient to the patient as it is readily available and adequate for surgical purposes.

FIGS. 1, 3, 4, and 5 illustrate a conventional spring-type hose or tube clamp 31 designed to slide along and around a hollow, pliable tube 20 coupled to the open proximal end 13 of tube 12 by coupler 19. Shown in its open position in FIGS. 1, 3, and 5, clamp 31 is closed by pressing the top leaf spring element 32 toward the bottom element 33, thereby squeezing tube 20 between the two jaws 34 and 35. Clamp 31 is held in its closed position by latch 36 when the tip 37 of leaf spring element 32 is forced to pass below latch 36. The flexible tube 20 is thereby closed and remains sealed until the latch 36 releases tip 37.

Alternatively, the open proximal end 13 of tube 12 may be provided with a manually controllable valve means, such as a stopcock (not shown). The stopcock may have a hollow, open proximal end shaped as a connector fitting to receive a conventional medical syringe. The connector fitting may be of the conventional "Luer" female type 21. The hollow, open distal end of the stopcock may be tapered and fitted within the open proximal end 13 of tube 12. The stopcock may include a vertical shaft extending perpendicularly through the valve between its open proximal and distal ends. The vertical shaft may be attached to a handle to enable the vertical shaft to be rotated about a vertical axis. The stopcock would generally be in its open position when the handle is aligned with the introducer 11.

An alternative valve of the "one-way" type may also be used, having a tapered, hollow, open proximal end; a tapered, open distal end; and an internal, resilient plunger or ball that normally closes the passage between the open proximal and distal ends. The conventional medical syringe of the piston-and-cylinder type is designed to attach to the open proximal end and press against the internal, resilient plunger to open the valve. Fluid under pressure from the syringe then passes through valve into hollow tube 12. Upon detachment of the syringe, the internal resilient plunger returns to its normally closed position, thereby sealing the passage between open proximal and distal ends and closing the end of tube 12.

Figure 3:
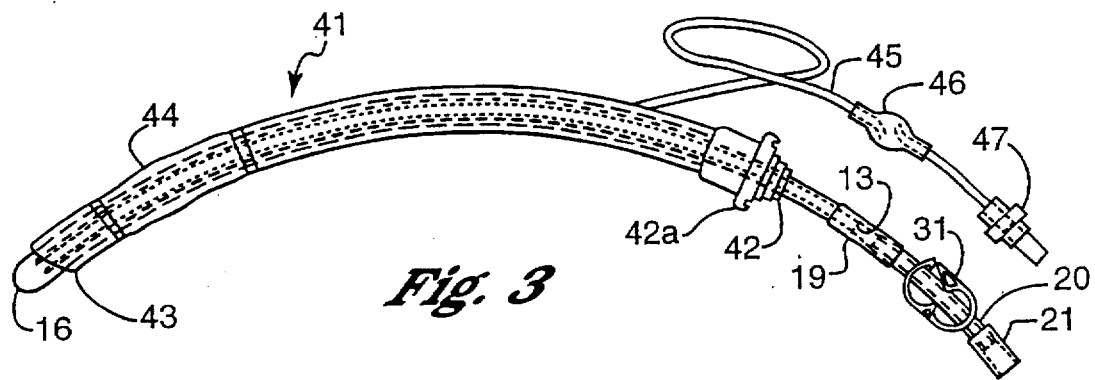
FIG. 3 shows in plan view an uninflated introducer with an uninflated, cuffed, endotracheal catheter.
Figure 4:
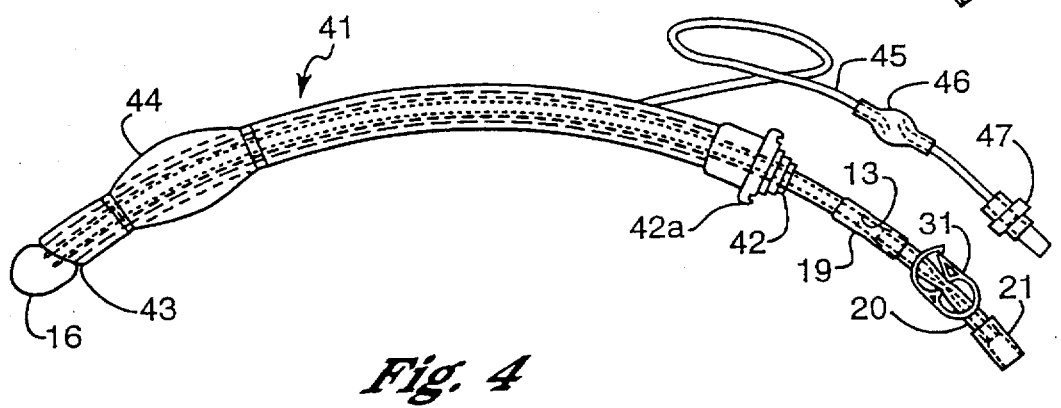
FIG. 4 shows in plan view an inflated introducer with an inflated, cuffed, endotracheal catheter.

FIGS. 3 and 4 illustrate the inflatable introducer 11 of the present invention installed within a cuffed catheter 41. Catheter 41 includes an open proximal end 42 having an external connector 42a for better manageability and greater airflow. At the opposite end is a beveled, open distal end 43. Alternatively, the open distal end 43 may be square and blunt so as to provide a uniform shoulder for the tip 16 of inflatable sheath 15. Introducer 11 is placed within catheter 41 such that the closed, smooth and rounded tip 16 of sheath 15 protrudes beyond the open distal end 43. The open distal end or tip 14 of tube 12 remains inside the open distal end 43 of catheter 41, as shown. To aid the placement of the closed, smooth and rounded tip 16 in the correct position, the rounded tip 16 may be marked by a band (not shown) to be aligned with the distal end 43 of catheter 41.

Endotracheal catheter tube 41 includes a thin, cylindrical cuff 44 affixed to the outer cylindrical portion of tube 41 near its open distal end 43. The interior of cuff 44 is coupled to a small, flexible pilot tube 45, a portion of which is embedded within the wall of endotracheal tube 41, and through a conventional pilot balloon 46 to an inflation valve connector 47.

Cylindrical sheath 15 is in its noninflated condition when inserted into and through catheter 41. Approximately two thirds of its upper length may remain inside the distal end portion of catheter 41, as shown. Clamp 31, coupled to the open proximal end 13 of tube 12 by coupler 19, is situated outside the open proximal end 42 of catheter 41 and is in its open position. The assembly of catheter, inflatable introducer with sheath, and fluid flow control means, as shown in FIG. 3, is in condition for inflation of sheath 15.

Note should be taken that the structures shown in FIGS. 3 and 4 have been presented in an "upside-down" or "flipped-over" form. Generally, such endotracheal tubes are inserted into the patient with the distal end 43 of the catheter pointing in an upwardly direction. When standing over the head of the patient, the physician may then intubate the patient with catheter 41.

FIG. 4 illustrates the inflatable introducer 11 installed in a cuffed catheter 41 and in its inflated condition. Closed, smooth, and rounded tip 16 of sheath 15, protruding beyond the open, distal end 43, is inflated to a diameter equal to or slightly larger than the outer diameter of catheter 41, as shown. The beveled distal end, or tip, 43 provides a surface against which inflated tip 16 of sheath 15 may bear as catheter 41 is intubated.

Approximately two thirds of the length of sheath 15 situated within the distal end portion of catheter 41 is also inflated to embrace and contact the inner cylindrical wall portion of the distal end of catheter 41. The physical contact between the expanded two-thirds portion of sheath 15 with the inner cylindrical wall of catheter 41 anchors and holds inflatable sheath 15 against any sliding or twisting movement as catheter 41 is intubated. Distal tip 14 of hollow tube 12 remains inside the distal end of catheter 43 in the inflated condition of sheath 15 as a precaution against any likelihood of rupture of sheath 15 by distal tip 14.

Clamp 31, coupled to the proximal end 13 of tube 12, is shown in its closed position, is thereby closing and sealing tube 12. Sheath 15 is thereby maintained in its inflated condition as catheter 41 with closed, smooth and rounded tip 16 is intubated into the passageway of a patient. Following intubation, clamp 31 is opened to release fluid pressure within tube 12 and sheath 13. Introducer 11 is then withdrawn from catheter 41.

Clamp 31, coupled to the open proximal end 13 of tube 12, is in the open position, as shown in FIG. 3. In this position, tube 12 is open and the assembled appliance may be packaged and sealed in an envelope to be sterilized by the conventional ethylene oxide process of gas sterilization or by any other medically acceptable radiation process.

The invention provides an improved procedure for the intubation of catheters and endotracheal tubes by providing a smooth, soft, rounded and pliable guiding tip for entering and enlarging the passageway to be intubated. This pliable guiding tip is made more accessible and controllable by the addition of malleable, shape-retaining tubing. Injury and trauma to the patient are reduced and better, more controllable intubation is achieved. The inflatable sheath 15 of the introducer 11 is readily inflated after rupturing the seals of the sterilized package while the catheter 41 and introducer 11 remain completely inside the package. The manually controllable clamp 31 is available for easy access to the physician to facilitate inflation and closure. Following removal of the assembled and inflated appliance, the smooth, soft and rounded tip 16 may be lubricated, by the physician, along with the outer cylindrical surface of the catheter 41, and the appliance is prepared for intubation. Following intubation, the clamp 31 is opened to release fluid pressure and deflate the sheath 15. The introducer with sheath is then withdrawn and discarded.

As contemplated for the embodiment of the present invention shown in FIGS. 1–4, an exemplary introducer 11 could be constructed as follows. Beginning with a length of dead-soft 3003 aluminum tubing, the tubing is annealed, chamfered, and straight with no burrs or sharp edges. The inner diameter may be approximately 0.019 inches plus or minus 0.002 inches. The outer diameter may be 0.047 inches plus or minus 0.002 inches. The length of the tube may be 12.0 inches plus or minus 0.12 inches. After such a dead-soft aluminum tube has been obtained, the entire length may be wiped with methyl ethyl ketone. The sheath and coupler may then be connected by adhesives to the tube 12. Clamp 31 and pliable tube 20 with connector fitting 21 may then be affixed to the coupler 19 and, as appropriate, with adhesive.

Alternatively, the hollow tube 12 may be made of the same annealed 3003 aluminum with the following inner dimensions with the same respective tolerances: inner diameter 0.075 inches; outer diameter 0.125 inches; and a length of 15.0 inches.

Figure 5:
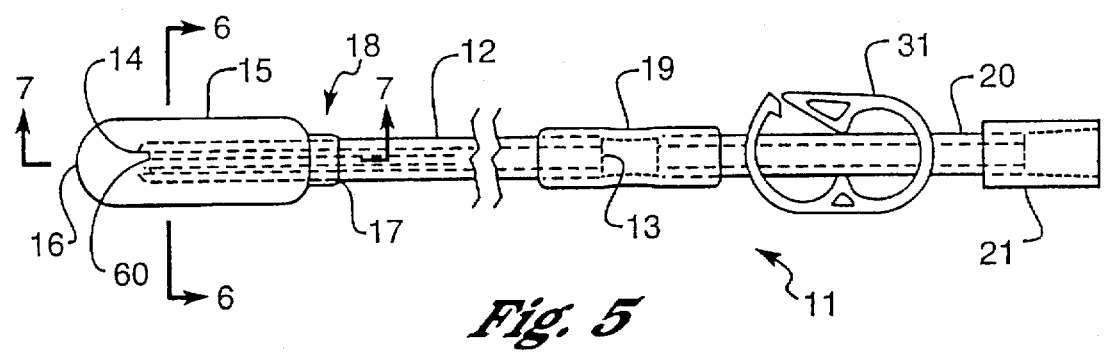
FIG. 5 shows in plan view a second embodiment of the present invention, having a malleable tip.
Figure 6:
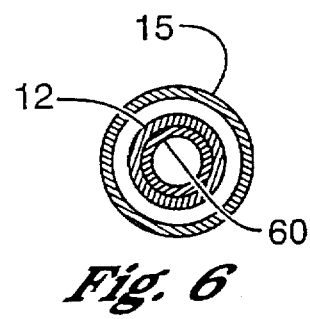
FIG. 6 shows a cross-section view of the tip of the embodiment of FIG. 5 along the line 6—6 of FIG. 5.
Figure 7:
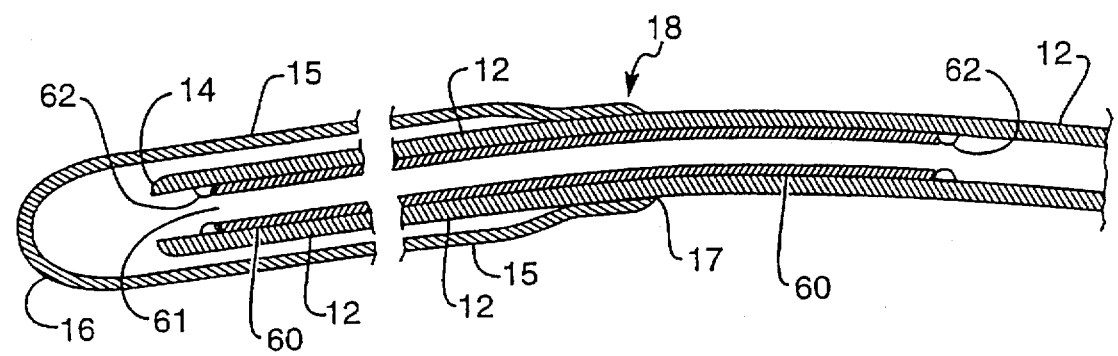
FIG. 7 shows in cross-section the end tip of the embodiment shown in FIG. 5 along line 7—7 of FIG. 5.

As shown in FIGS. 5–7, a second embodiment of the present invention includes the use of a malleable hollow tube 60 adjacent the open distal end 14 of the introducer tube 12. Those structures in FIGS. 5–7 which are the same as those in FIGS. 1–4 are designated by the same or similar reference numbers. The end of the hollow malleable tip 60 most proximal to the clamp 31 is in fluidtight engagement with the introducer tube 12 and may be enveloped by it. The distal end 61 of the hollow malleable tip 60 is surrounded by material tending not to have sharp edges so that the sheath surrounding the distal end 16 or sheath 15 of the introducer 11 is not punctured by coming into contact with any sharp edges. In order to ensure that the malleable metal tip 60 does not damage or injure the sheath 15, the hollow malleable tip 60 may be inserted into the flexible introducer tube 12 such that the distal end 61 of the malleable tip 60 is several millimeters within the distal end 14 of the introducer tube 12. The sheath 15 then extends several millimeters beyond the distal end 14 of the introducer tube 12.

For materials subject to destructive oxidation and/or corrosion, such as copper and the like, the malleable metal may be entirely encased in plastic both within and without while maintaining the hollow tubular and malleable features of this structure and metal. Alternatively, and as best shown in FIG. 7, drops of glue 62 may be used to secure the malleable tip 60 within the flexible introducer tube 12. Alternatively, the malleable tip may be subject to surface treatment as by electroless nickel in order to inhibit corrosion and enhance adhesion.

An exemplary malleable tip 60 could be constructed as follows. Using dead-soft C12200 annealed or equivalent copper with an approximate tensile strength of 30 kPSI and an approximate yield of 11 kPSI as available from Copper Development Associates, all burrs and sharp edges are removed from the malleable tip. The length of the malleable tip 60 is approximately 3.0 inches plus or minus 0.1 inches with possible inner or outer diameters of 0.028 inches and 0.071 inches, respectively, and with tolerances of plus or minus 0.002 inches.

Alternatively, an inner diameter of 0.031 inches and an outer diameter of 0.081 inches plus or minus 0.002 inches may also be used advantageously. Once the malleable tip 60 has been prepared, drops of glue 62 may be placed inside the flexible introducer tube 12 and cured after insertion of the malleable tip 60. The remaining structures associated with the introducer tube 11 may then be affixed in a manner similar to that for the malleable tube 12 embodiment set forth above.

In operation, the embodiment of the present invention where the entire introducer tube 12 is malleable, as shown in FIGS. 1–4, proceeds as follows. Initially, the introducer tube 12 is straight or conforms to the initial curvature of the catheter 41. From this geometry, if the introducer 11 has not previously been inserted into the catheter 41, the introducer 11 is easily inserted into the catheter 41 so that the tip 16 extends beyond the open distal end 43 of the catheter per the procedure set forth previously. Once the introducer 11 has been secured within the catheter 41 after inflation, the frictional engagement between the inflated sheath 15 and the catheter interior will hold the introducer 11 in place relative to the catheter 41 while the malleable introducer tube 12 is bent to the physician's preferred configuration. The physician may accomplish this by hand, bending the tube into almost any configuration so long as the bends are not too severe. The fluid flow through the hollow introducer tube should not be obstructed nor should any breach be created in the wall of the hollow introducer tube. The frictional engagement between introducer 11 and catheter 41 is sufficient to keep the catheter and introducer from turning with respect to one another during the configuration process or intubation.

Once the introducer tube 12 has been bent to the physician's preferred configuration, the catheter 41, having also adopted this configuration, is intubated into the patient. As the inflated introducer end 16 and catheter 41 are lubricated with an anesthetizing or other appropriate type of lubricant (such as Lubafax jelly), passage of the catheter 41 into the patient's mouth or nose is made easier. The shape of the catheter 41, as dictated by the malleable introducer tube 12, can be such that the distal introducer end 16 tends to press against anatomical structures that serve to guide the introducer tip 16 into the patient without trauma and avoiding obstruction.

If an obstruction is encountered by the inflated introducer tip 16, the physician may gently bend the malleable introducer tube 12 against a stationary object such as the physician's hand or fingers or any anatomical structure of the patient that would not be traumatized by the force generated from the bending process. Sometimes, when the inflated introducer tip 16 is obstructed during intubation, it may be possible to avoid the obstruction and proceed with intubation by slightly withdrawing the catheter-introducer pair and bending the malleable introducer tube 12 so that the tip 16 adopts a different attitude with respect to the obstruction. Due to the lubricated and curved nature of the inflated introducer tip 16, the inflated introducer tip 16 may then approach the obstruction and find clear passage past it or may be pushed to one side by the obstruction so that the catheter 41 may proceed past the obstruction.

With respect to the second embodiment of the present invention where the introducer tube 12 remains flexible and only the tip of the introducer tube is malleable, the physician may bend the malleable tip 60 to a preferred configuration prior to or after inflation of the introducer tip 16 and secure the introducer 11 by such inflation to the interior of the catheter. Bending the malleable tip 60 prior to insertion of the introducer 11 into the catheter 41 should be avoided as it may prevent easy passage of the malleable tip into the catheter. Once the catheter portion surrounding the malleable tip has adopted the configuration preferred by the physician, the catheter-introducer pair may then be inserted into the patient.

As indicated above the indication of specific inner and outer diameters for the hollow tube 12 and the malleable tip 60, the width of the wall surrounding the malleable portion of the present invention is on the same order as that of its opening 14, 61 into the sheath 15. The similarities in the wall width and the opening diameter provides the structural support necessary to allow the hollow tube 12 or tip 60 to resist deformation during intubation to provide support, yet malleably deforms in the physician's hands prior to or during intubation. Due to the relative similarities of the openings 14, 61 and their associated wall thicknesses, the hollow tube 12 and the malleable tip 60 resist buckling and kinking.

With an inner diameter of 0.019 inches and an outer diameter of 0.047 inches, the wall thickness of the hollow tube 12 such an introducer is 0.014 inches. With an inner diameter of 0.075 inches and an outer diameter of 0.125 inches, the hollow tube 12 has a wall thickness of 0.025 inches. In both instances, the diameter of the opening 14 of the hollow tube 12 is on the order of the wall thickness.

For the malleable tip 60, an inner diameter of 0.028 inches and an outer diameter of 0.071 inches provides a wall with a thickness of 0.022 inches. An inner diameter of 0.031 inches and an outer diameter of 0.081 inches provides a wall of thickness 0.025 inches. In both instances, the diameter of the opening 61 of the malleable tip 60 is on the order of the wall thickness.

While the present invention has been described with regards to particular embodiments, it is recognized that additional variations of the present invention may be devised without departing from the inventive concept.

What I claim is:

1. An inflatable introducer for insertion into a catheter for allowing easier intubation of the catheter into a patient's body, comprising:

an elongated, malleable metal tube having open proximal and distal ends and being at least long enough for intubation purposes, said malleable metal tube being susceptible to re-shaping by a human hand and tending to resiliently maintain a selected and attained shape before and after insertion into said catheter and during intubation, said malleable metal tube resisting buckling and kinking;

a cylindrical, elongated, inflatable sheath surrounding and enclosing a distal end portion and said open distal end of said malleable metal tube;

fluid flow control means for controllably controlling the flow of fluid to and from said inflatable sheath, said fluid flow control means being coupled in fluidtight engagement to said open proximal end of said malleable metal tube; and adapter means for receiving a source of pressurized fluid for inflating said inflatable sheath, said adapter means being coupled in fluidtight engagement with said fluid flow control means;

said open distal end having a diameter on the same order as a wall thickness of said malleable metal tube; whereby said malleable metal tube providing means for resisting deformation during intubation yet malleably deforms during manual manipulation prior to and during intubation.

2. The introducer in accordance with claim 1 wherein said elongated, malleable metal tube extends a distance at least equal to the length of said catheter.

3. The introducer in accordance with claim 1 wherein said elongated, malleable metal tube has an inert, tightly fitting and open-ended cover preventing oxidation or other reactions of said malleable metal tube.

4. The introducer in accordance with claim 3 wherein said elongated, malleable metal tube extends a first distance from said cylindrical, elongated, inflatable sheath approximately the same as a second distance into said cylindrical, elongated, inflatable sheath.

5. The introducer in accordance with claim 3 wherein said elongated, malleable metal tube is made of dead-soft 3003 aluminum tubing having an inner diameter of approximately nineteen thousandths inch (0.019") and an outer diameter of approximately forty-seven thousandths inch (0.047").

6. The introducer in accordance with claim 3 wherein said elongated, malleable metal tube is made of dead-soft 3003 aluminum tubing having an inner diameter of approximately seventy-five thousandths inch (0.075") and an outer diameter of approximately one hundred twenty-five thousandths (0.125").

7. The introducer in accordance with claim 3 wherein said elongated, malleable metal tube is made of dead soft C12200 copper having an inner diameter of approximately twenty-eight thousandths inch (0.028") and an outer diameter of approximately seventy-one thousandths inch (0.071").

8. The introducer in accordance with claim 3 wherein said elongated, malleable metal tube is made of dead soft C12200 copper having an inner diameter of approximately thirty-one thousandths inch (0.031") and an outer diameter of approximately eighty-one thousandths inch (0.081").

9. In a soft, inflatable introducer adapted to be inserted into a hollow, cylindrical endotracheal catheter having open proximal and distal ends, the introducer being positioned and inflated to aid the intubation of the endotracheal catheter into a laryngotracheal passageway of a patient, and being deflated and withdrawn following intubation, comprising in combination:

(a) a long, hollow tube having open proximal and distal ends, said hollow tube having an external diameter less than the inside diameter of the hollow endotracheal catheter with which it is to be used, and having a length approximately equal to the length of the hollow endotracheal catheter;

(b) a cylindrical, elongated, inflatable sheath surrounding and enclosing the distal end portion and the open distal tip of said hollow tube, said inflatable sheath being composed of thin, soft and pliable material and having a sealed, smooth, rounded tip portion; said sheath being elongated and cylindrical in shape in its noninflated condition and the smooth, round tip portion being spaced apart from the open distal tip of said hollow tube approximately one-third of the length of the sheath when in its noninflated condition, the end portion of said cylindrical, inflatable sheath opposite the smooth, rounded tip portion being securely attached to the outside cylindrical surface of said hollow tube for forming a fluidtight seal between the inside of said inflatable sheath and the distal end portion of said hollow tube, the outer diameter of said thin, cylindrical, elongated sheath being larger than the external diameter of said long, hollow tube and being less than the inside diameter of the hollow endotracheal catheter; said cylindrical sheath and the distal end portion of said hollow tube being adapted for insertion into the hollow endotracheal catheter with the smooth, rounded tip portion of said inflatable sheath protruding beyond the open distal end of the hollow endotracheal catheter, the open proximal end portion of said hollow tube being adapted for receiving fluid of sufficient pressure to expand said cylindrical, inflatable sheath situated within the distal end portion of the hollow endotracheal catheter to a diameter at least as large as the inside diameter of the hollow endotracheal catheter to provide physical contact between the outer cylindrical surface of said thin, elongated sheath and the inner cylindrical surface of the distal end portion of the hollow endotracheal catheter, the expansion of said cylindrical inflatable sheath by fluid under pressure causing the smooth, rounded tip portion protruding beyond the open distal end of the hollow endotracheal catheter to expand to a diameter approximately equal to the outside diameter of the hollow endotracheal catheter; and (c) means associated with the open proximal end portion of said hollow tube for closing the open proximal end portion of said hollow tube after said inflatable sheath has been inflated to hold and maintain said sheath in its expanded condition to prevent sliding of said cylindrical, elongated sheath relative to the hollow endotracheal catheter as the catheter is being intubated, the inflated smooth rounded tip portion of said inflatable introducer having a soft, pliable, fluid-filled cushion ahead of the distal end of the hollow endotracheal catheter for entry into a patient's laryngotracheal passageway through which the hollow endotracheal catheter is to be intubated, the improvement wherein:

said long, hollow tube is of thick-walled metal with a range of malleability accommodating varied-sized endotracheal tubes as catheters for different-sized patients, said thick walls of said long, hollow metal tube resisting buckling and kinking when bent;

said open distal tip having a diameter on the same order as said thick walls of said long, hollow metal tube; whereby said long hollow metal tube providing means for resisting deformation during intubation yet malleably deforms during manual manipulation prior to and during intubation.

10. The soft, inflatable introducer adapted to be inserted into a hollow, cylindrical endotracheal catheter of claim 9, further comprising:

said thick-walled and malleable metal being aluminum.

11. The soft, inflatable introducer adapted to be inserted into a hollow, cylindrical endotracheal catheter of claim 9, wherein said thick-walled and malleable metal tube has an inert, tightly fitting and open-ended cover that prevents oxidation or other reactions of said malleable metal tube.

12. The introducer in accordance with claim 11 wherein said thick-walled and malleable metal tube is made of dead-soft 3003 aluminum tubing having an inner diameter of approximately nineteen thousandths inch (0.019") and an outer diameter of approximately forty-seven thousandths inch (0.047").

13. The introducer in accordance with claim 11 wherein said thick-walled and malleable metal tube is made of dead-soft 3003 aluminum tubing having an inner diameter of approximately seventy-five thousandths inch (0.075") and an outer diameter of approximately one hundred twenty-five thousandths inch (0.125").

14. The introducer in accordance with claim 11 wherein said thick-walled and malleable metal tube is made of dead soft C12200 copper having an inner diameter of approximately twenty-eight thousandths inch (0.028") and an outer diameter of approximately seventy-one thousandths inch (0.071").

15. The introducer in accordance with claim 11 wherein said thick-walled and malleable metal tube is made of dead soft C12200 copper having an inner diameter of approximately thirty-one thousandths inch (0.031") and an outer diameter of approximately eighty-one thousandths inch (0.081").

16. An inflatable introducer for insertion into a catheter for allowing easier intubation of the catheter into a patient's body, comprising:

an elongated, malleable metal tube having open proximal and distal ends and being at least long enough for intubation purposes, said malleable metal tube being susceptible to re-shaping by a human hand and tending to maintain a selected attained shape before and after insertion into said catheter and during intubation, said malleable metal tube having a relatively thick wall to thereby decrease the amount of fluid necessary to inflate said inflatable sheath and to prevent buckling during use, said malleable metal tube extending a distance at least equal to the length of said catheter;

a cylindrical, elongated, inflatable sheath surrounding and enclosing a distal end portion and said open distal end of said malleable metal tube;

fluid flow control means for controllably controlling the flow of fluid to and from said inflatable sheath, said fluid flow control means being coupled in fluidtight engagement to said open proximal end of said malleable metal tube; and adapter means for receiving a source of pressurized fluid for inflating said inflatable sheath, said adapter means being coupled in fluidtight engagement with said fluid flow control means;

said open distal end having a diameter on the same order as said relatively thick wall of said malleable metal tube; whereby said malleable metal tube providing means for resisting deformation during intubation yet malleably deforms during manual manipulation prior to and during intubation.

17. An inflatable introducer for insertion into a catheter for allowing easier intubation of the catheter into a patient's body, comprising:

an elongated, malleable metal tube having open proximal and distal ends and being at least long enough for intubation purposes, said malleable metal tube being susceptible to re-shaping by a human hand and tending to maintain a selected and attained shape before and after insertion into said catheter and during intubation, said malleable metal tube having an inert, tightly fitting and open-ended cover preventing oxidation or other reactions of said malleable metal tube;

a cylindrical, elongated, inflatable sheath surrounding and enclosing a distal end portion of said open distal end of said malleable metal tube, said malleable metal tube extending a first distance from said cylindrical, elongated, inflatable sheath approximately the same as a second distance into said cylindrical, elongated, inflatable sheath;

fluid flow control means for controllably controlling the flow of fluid to and from said inflatable sheath, said fluid flow control means being coupled in fluidtight engagement to said open proximal end of said malleable metal tube; and adapter means for receiving a source of pressurized fluid for inflating said inflatable sheath, said adapter means being coupled in fluidtight engagement with said fluid flow control means;

said open distal end having a diameter on the same order as a wall thickness of said malleable metal tube; whereby said malleable metal tube providing means for resisting deformation during intubation yet malleably deforms during manual manipulation prior to and during intubation.

* * * * *